(12) United States Patent
Coussios et al.

(10) Patent No.: US 9,226,727 B2
(45) Date of Patent: Jan. 5, 2016

(54) ULTRASOUND SYSTEMS

(75) Inventors: Constantin Coussios, Oxford (GB);
Ronald Aurele Roy, Brighton, MA (US); Manish Arora, Oxford (GB); Jamie Collin, Oxford (GB); Gail Ter Haar, Oxford (GB); Sacha D. Nandlall, Oxford (GB); Edward Jackson, Oxford (GB)

(73) Assignee: Isis Innovation Limited, Summertown, Oxford (GB)

( * ) Notice: Subject to any disclaimer, the term of this patent is extended or adjusted under 35 U.S.C. 154(b) by 0 days.

(21) Appl. No.: 13/497,484

(22) PCT Filed: Sep. 22, 2010

(86) PCT No.: PCT/GB2010/051592
§ 371 (c)(1),
(2), (4) Date: Jun. 26, 2012

(87) PCT Pub. No.: WO2011/036485
PCT Pub. Date: Mar. 31, 2011

(65) Prior Publication Data
US 2012/0271169 A1    Oct. 25, 2012

(30) Foreign Application Priority Data
Sep. 22, 2009 (GB) ................... 0916635.6

(51) Int. Cl.
| | |
|---|---|
| A61B 8/00 | (2006.01) |
| A61M 37/00 | (2006.01) |
| A61N 7/02 | (2006.01) |
| A61B 17/00 | (2006.01) |
| A61B 18/00 | (2006.01) |
| A61N 7/00 | (2006.01) |

(52) U.S. Cl.
CPC .............. *A61B 8/00* (2013.01); *A61M 37/0092* (2013.01); *A61N 7/02* (2013.01); *A61B 2017/00084* (2013.01); *A61B 2018/00642* (2013.01); *A61B 2018/00666* (2013.01); *A61N 2007/0008* (2013.01); *A61N 2007/0039* (2013.01)

(58) Field of Classification Search
USPC .......................................... 600/437, 407, 439
See application file for complete search history.

(56) References Cited

U.S. PATENT DOCUMENTS

| | | |
|---|---|---|
| 5,158,071 A | 10/1992 | Umemura et al. |
| 6,508,774 B1 | 1/2003 | Acker et al. |

(Continued)

FOREIGN PATENT DOCUMENTS

| | | |
|---|---|---|
| WO | WO 02051501 A1 | 7/2002 |
| WO | WO 03/070105 A1 | 8/2003 |
| WO | WO 2009094554 A2 | 7/2009 |
| WO | WO 2010/052494 A1 | 5/2010 |

OTHER PUBLICATIONS

Tran et al., "Correlation Between Accoustic Backscatter Variability and Tissue Damage Produced by Pulsed Cavitational Ultrasound Therapy", Ultrasonics Symposium, 2004 IEEE Montreal, Canada, Aug. 23-27, 2004, vol. 2, pp. 1461-1464, Aug. 23, 2004.

(Continued)

*Primary Examiner* — Joel F Brutus
(74) *Attorney, Agent, or Firm* — Wegman, Hessler & Vanderburg

(57) ABSTRACT

A sensing system for sensing the condition of an object comprises a transducer arranged to generate pressure waves directed at the object and detection means, such as a pressure wave detector, arranged to detect cavitation or other processes in the object. The system further comprises processing means arranged to receive detection signals from the detection means, to process the detection signals to measure a signal parameter of the detection signals that varies with a parameter of the object, and may generate a sensor output that varies in response to changes in the signal parameter.

10 Claims, 8 Drawing Sheets

(56) References Cited

U.S. PATENT DOCUMENTS

| | | | |
|---|---|---|---|
| 2003/0093013 A1 | 5/2003 | Zhong et al. | |
| 2004/0082857 A1* | 4/2004 | Schonenberger et al. | 600/439 |
| 2004/0264293 A1* | 12/2004 | Laugharn et al. | 366/127 |
| 2006/0184075 A1 | 8/2006 | Restle et al. | |
| 2006/0264809 A1 | 11/2006 | Hansmann et al. | |
| 2007/0083120 A1* | 4/2007 | Cain et al. | 600/439 |
| 2007/0161902 A1 | 7/2007 | Dan | |
| 2007/0265560 A1 | 11/2007 | Soltani et al. | |

OTHER PUBLICATIONS

Rabkin, et al., "Hyperecho in Ultrasound Images of HIFU Therapy: Involvement of Cavitation", Ultrasound in Medicine and Biology, New York, NY, US, vol. 31, No. 7, pp. 947-956, Jul. 1, 2005.

Salgaonkar et al., "Image-Guided Ex Vivo Liver Ablation by Unfocused Ultrasound Using Passive Cavitation Detection", Proc. of SPIE, vol. 6440, 2007.

International Search Report and Written Opinion mailed Jan. 31, 2011 for PCT/GB/2010/051592 filed Sep. 22, 2010.

International Preliminary Examination Report on Patentability mailed Apr. 5, 2012 for PCT/GB2010/051592 filed Sep. 22, 2010.

International Search Report and Written Opinion mailed Feb. 10, 2011 for PCT/GB2010/051570 filed Sep. 20, 2010, which is the International Application of related U.S. Appl. No. 13/497,470, filed Jun. 26, 2012.

International Preliminary Report on Patentability mailed Apr. 5, 2012 for PCT/GB2010/051570 filed Sep. 20, 2010, which is the International Application of related U.S. Appl. No. 13/497,470, filed Jun. 26, 2012.

Communication Pursuant to Article 94(3) EPC mailed Feb. 19, 2013 for EP 10 768 050.6.

* cited by examiner

Fig. 3
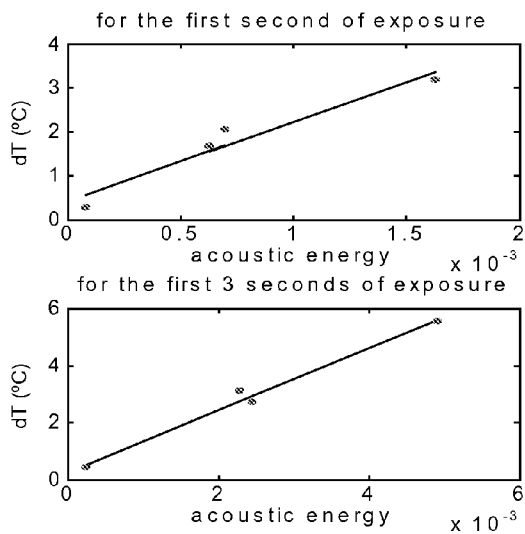
Fig. 4
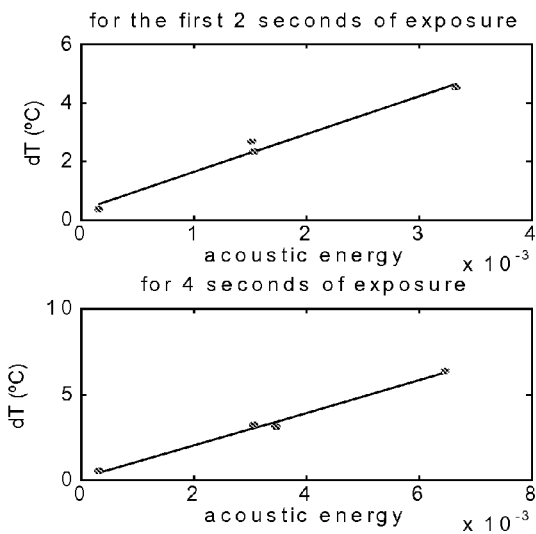
Fig. 5
Fig. 6
Fig. 7
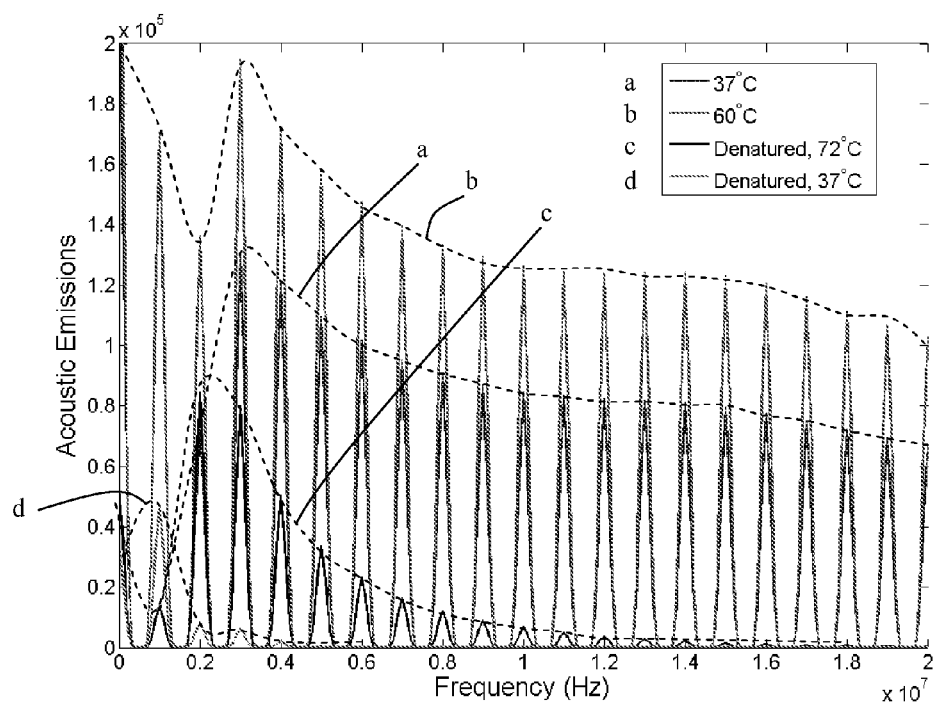

Fig. 11b
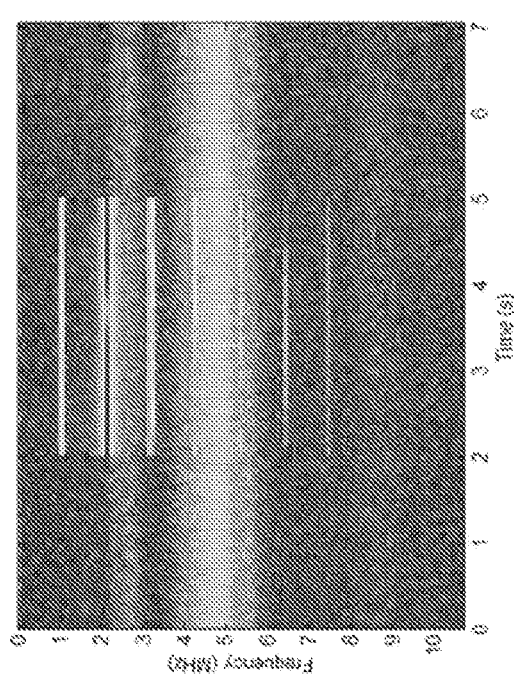
Fig. 11d
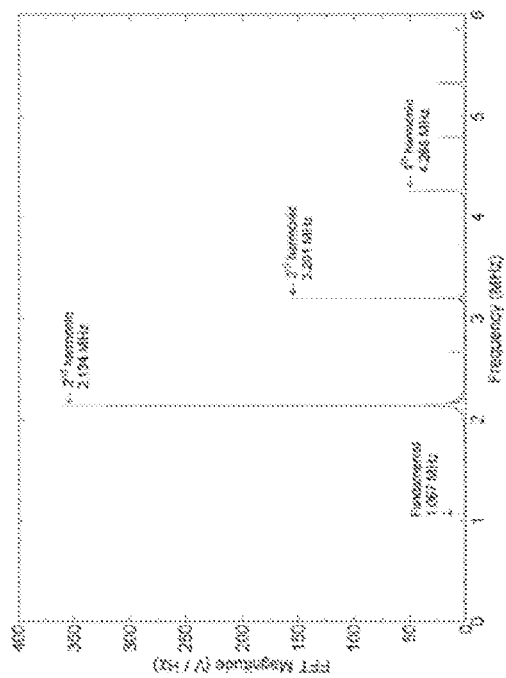
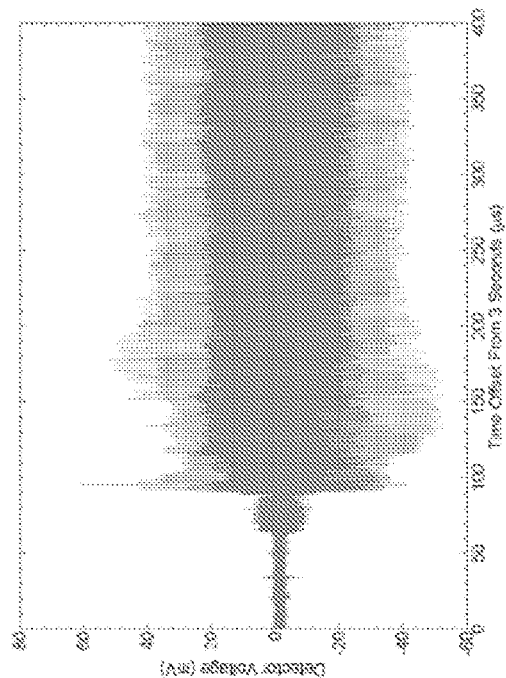
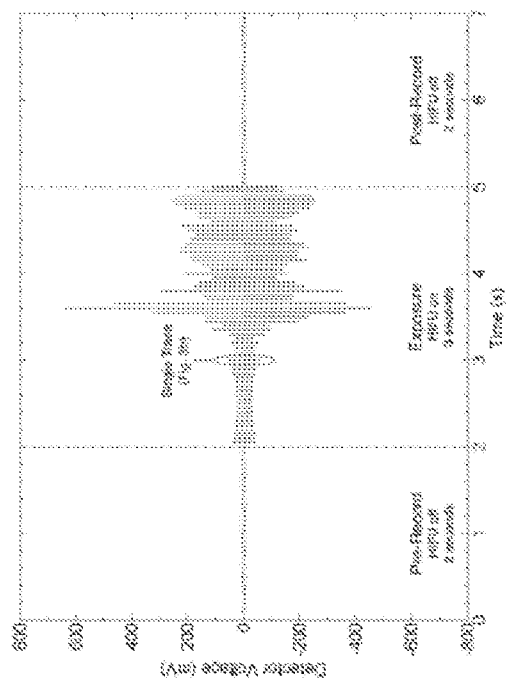
Fig. 11a
Fig. 11c

ULTRASOUND SYSTEMS

CROSS-REFERENCE TO RELATED APPLICATIONS

This application claims the priority filing benefit of International PCT Application PCT/GB2010/051592 filed Sep. 22, 2010 and published under PCT 21(2) in the English language; and Great Britain Patent Application Serial No. 0916635.6 filed Sep. 22, 2009.

FIELD OF THE INVENTION

The present invention relates to ultrasound systems and in particular to therapeutic ultrasound systems arranged to generate cavitation in tissue during therapy.

BACKGROUND TO THE INVENTION

Therapeutic ultrasound in general, and High-Intensity Focussed Ultrasound (HIFU) in particular, is rapidly emerging as a promising tool for non-invasive ablation of cancerous, diseased or fat tissue, and as a means of inducing localized heating for the purpose of hyperthermia-enhanced drug release.

For all of the above applications, a major factor limiting the use of therapeutic ultrasound is the lack of a technique that makes it possible to monitor changes in tissue properties at the ultrasound focus non-invasively.

When ultrasound is used to induce mild hyperthermia, the major effect at the ultrasound focus will be a mild increase in tissue temperature. When ultrasound is used to induce ablation, the primary effect will be a dramatic change in the viscoelastic properties of tissue (in a manner similar to cooking a steak).

Clinically available monitoring techniques include the use of B-mode pulse-echo ultrasound, which is only sensitive to changes in the acoustic impedance, speed of sound and attenuation of tissue; a major limitation of this technique is that it cannot be used during ultrasound exposure, because the signal from the therapy transducer will saturate that from the diagnostic transducer. Performing the procedure inside an MRI scanner is another clinically available alternative: MRI is capable of providing temperature measurements, albeit with poor spatio-temporal resolution, and is primarily prohibitive by virtue of its cost. Importantly for tissue ablation applications, it should be noted that temperature is an indirect indicator of tissue damage, and a more direct indicator is therefore desirable.

Under the right conditions, an ultrasound wave propagating through tissue will excite micron-sized bubbles, a phenomenon known as acoustic cavitation. These bubbles can either be spontaneously nucleated by the ultrasound, by making use of gas dissolved in the surrounding tissue, or injected intravenously, such as by using ultrasound contrast agents.

SUMMARY OF THE INVENTION

The present invention provides a sensing system for sensing the condition of an object, the system comprising a pressure wave source, which may comprise a transducer, arranged to generate pressure waves directed at the object, detection means arranged to detect cavitation in the object, and processing means. The processing means may be arranged to receive detection signals from the detection means. The processing means may be arranged to measure a signal parameter of the detection signals, and preferably one that varies with a parameter of the object. The processing means may be arranged to generate a sensing output that varies in response to changes in the signal parameter.

The pressure waves may be ultrasound or audible sound waves.

The sensing output may be arranged to control the transducer so as to vary the output of the transducer in response to changes in the sensing output.

Alternatively, or in addition, the system may further comprise user feedback means, such as a display or an audio or tactile feedback device, arranged to provide feedback to a user. The sensing output may be arranged to control the user feedback means and to vary the feedback in response to changes in the sensing output.

The processing means may be arranged to define a target range of the signal parameter, and to change the sensing output in response to the signal parameter being outside the target range. For example the range may be defined by a maximum value, for example of temperature, or both a maximum and minimum value.

The detection means may comprise at least one pressure wave detector arranged to detect pressure waves generated by the cavitation. For example this may be a pressure transducer. Alternatively other types of detection device or system can be used, for example imaging systems arranged to image the cavitation.

The parameter of the object may be temperature. The signal parameter may be arranged to vary with the level of cavitation activity in the object, as that is indicative of the temperature of the object. The signal parameter may be the variance of the detection signals.

The processing means may be arranged to generate a control output to control the transducer. This may be the sensing output, or it may be a separate output.

The processing means may be arranged to vary the control output over time. For example the control signal driving the transducer may be varied to increase the peak pressure of the pressure waves. With or without this control, the processing means may be arranged to monitor how the signal parameter changes in response to changes in the transducer output, which in turn may be measured or determined from the drive signal to the transducer or from any control input to the transducer. The pressure at which cavitation begins may thus be determined. The timing of the detector output changes, which is indicative of the cavitation threshold pressure, can then be used as the signal parameter on which variation of the sensing output is based. Alternatively the signal parameter can be measured for various different transducer outputs over time, and those measured values used to determine the threshold pressure.

The parameter of the object may be a viscoelastic parameter. The signal parameter may be a parameter of the frequency content of the detection signals.

The present invention further provides a method of sensing the condition of an object, the method comprising generating pressure waves directed at the object, detecting cavitation in the object using detection means arranged to output detection signals, monitoring a signal parameter of the detection signals that varies with a parameter of the object, and generating a sensing output that varies in response to changes in the signal parameter.

In some embodiments of the present invention the broadband emissions generated by cavitating bubbles either during or after therapeutic ultrasound exposure can be used to measure properties of tissue, such as temperature (in the context of mild hyperthermia in a homogenous medium such as fat) or as a direct indicator of changes in viscoelastic properties of tissue. The principle is readily extendable to other materials and other non-medical applications.

The present invention further provides a sensing system for sensing the condition of an object, the system comprising a pressure wave source, which may comprise a transducer, arranged to generate pressure waves directed at the object, a pressure wave detector arranged to detect pressure waves coming from the object. The detector may be arranged to output detection signals. The system may further comprise processing means which may be arranged to receive the detection signals, and may be arranged to process the detection signals, optionally to measure a signal parameter of the detection signals that varies with a parameter of the object. The processing means may be arranged to generate a sensor output that varies in response to changes in the signal parameter.

The parameter of the detection signals may be a parameter of the spectral content of the detection signals. For example it may be, or be a measure of, the magnitude of one or more frequency components of the detection signals, for example an absolute or relative magnitude. Alternatively the parameter may be any of those referred to above.

The transducer may be arranged to generate pressure waves at an insonation frequency and the parameter of the detection signals may be a measure of the component of the detection signals at at least one harmonic, which may be a any type of harmonic including a subharmonic or ultraharmonic, of the insonation frequency.

The processing means may be arranged to monitor the parameter of the detection signal over time and to identify minima or maxima of the parameter of the detection signal. For example the processing means may be arranged to define a condition which, if met, indicates that a minimum, or maximum, or other variation, of the parameter has occurred.

The present invention further provides a method of sensing the condition of an object, the method comprising generating pressure waves directed at the object, detecting pressure waves coming from the object using a detector arranged to output detection signals, and processing the detection signals to measure a signal parameter of the detection signals that varies with a parameter of the object. The method may comprise generating a sensor output that varies in response to changes in the signal parameter.

Preferred embodiments of the present invention will now be described by way of example only with reference to the accompanying drawings.

BRIEF DESCRIPTION OF THE DRAWINGS

FIGS. 3 to 6 are graphs showing correlation of cavitation emissions with temperature rise in porcine subcutaneous fat;

FIG. 7 is a graph showing computationally calculated changes in the spectral content of noise emissions produced by a 1-micron single bubble excited at 1 MHz for different levels of denaturation and different temperatures of the surrounding tissue;

FIG. 11a is a plot of detector voltage as a function of time acquired using the system of FIG. 10;

FIG. 11b is a higher resolution trace of part of the plot of FIG. 11a;

FIG. 11c is a plot of the spectral content of the trace of FIG. 11b;

FIG. 11d is a spectrogram showing the spectral content of the detector voltage as a function of time;

DESCRIPTION OF THE PREFERRED EMBODIMENTS

Figure 1:
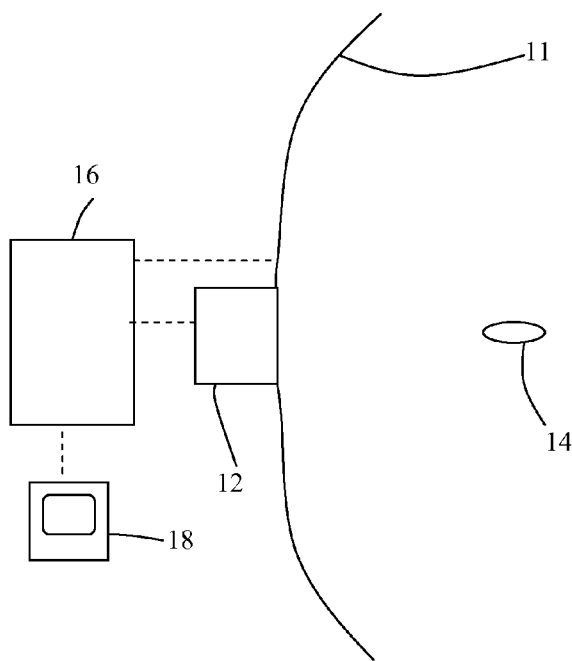
FIG. 1 is a diagram of a therapeutic ultrasound system according to an embodiment of the invention.

Referring to FIG. 1, a high intensity focused ultrasound system according to an embodiment of the invention comprises a high intensity focused ultrasound (HIFU) transducer 11 with a coaxial passive cavitation detector (PCD) 12 mounted at its centre. The ultrasound transducer 11 has a focal point 14 at which the ultrasound it produces is at the highest intensity and tissue to be treated is therefore located in a volume at and around that focal point 14. The PCD 12 comprises an ultrasound detector which is a pressure sensor arranged to output a signal having a voltage that varies with the pressure it detects. The pressure varies at the frequency of the ultrasound detected, and the sensor may include a high pass filter so as to avoid saturation by signals at the frequency of the ultrasound transducer 11, which can be around 1 MHz, being most sensitive to signals with a frequency range significantly higher than the frequency of the ultrasound transducer 11, for example around 5 to 15 MHz, which makes it sensitive to the acoustic emissions associated with inertial cavitation.

A controller 16 is arranged to drive the ultrasound transducer 11 using a drive signal. This drive signal is generated by an oscillator and has a frequency which determines the frequency of the ultrasound generated, and an amplitude which determines the intensity of the ultrasound generated. It is also pulse width modulated, and the controller is arranged to vary the pulse width and duty ratio (and hence pulse frequency) of the drive pulses that generate pulses of ultrasound from the transducer 11. The controller 16 is also arranged to receive detection signals which are the output voltage from the PCD 12 and to vary the drive signal in response to changes in the detection signals. The controller 16 is also connected to a display 18 and is arranged to analyze the signals received from the PCD 12 to obtain information, and to output a display control signal arranged to control the display 18 to display that information.

When cavitation occurs in tissue or another object, for example produced by an ultrasound system like the system of FIG. 1, as a bubble collapses under the effect of an ultrasound field, it reradiates sound in a manner that is directly dependent on the local temperature and the rheological and mechanical properties of its surroundings. This means that the bubble or bubbles effectively act as point sensors which radiate information about the medium that surrounds them. Collecting this information using a single-element pressure sensor 12 or an array of cavitation detectors (ultrasound transducers used as receivers), and post-processing the signal received by such detectors in the time and frequency domain, makes it possible to relate changes in signal levels to changes in properties of the object, and hence to monitor changes in the properties of the object and control operation of the ultrasound system.

Figure 2:
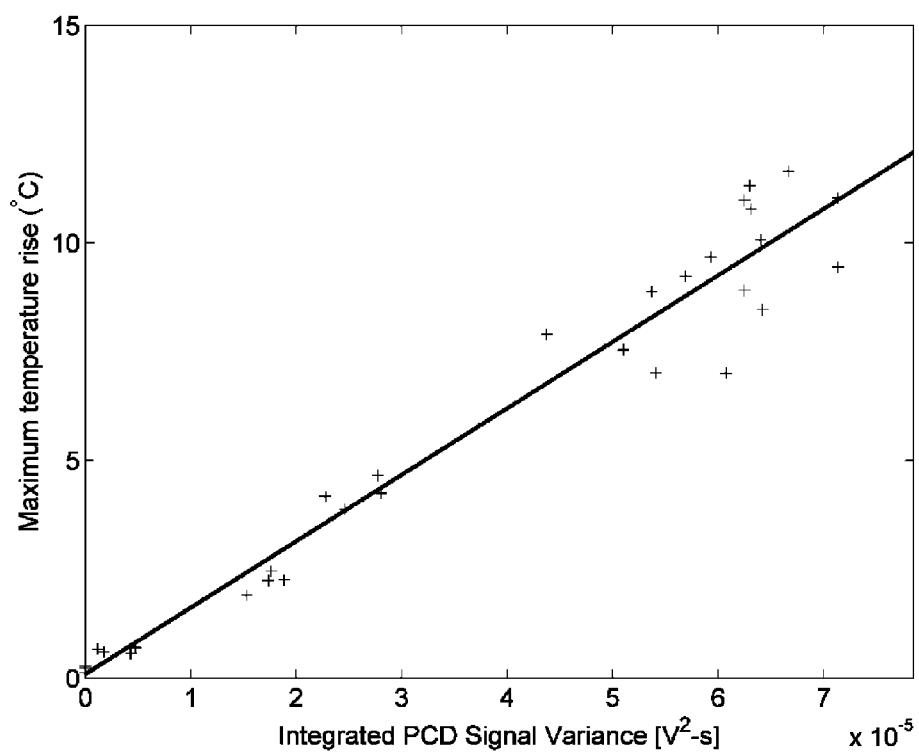
FIG. 2 is a graph showing the variation in temperature rise in a subject as a function of ultrasound detector signal variance.

Referring to FIG. 2, the output voltage V of the detector 12 varies at the frequency of ultrasound that it detects. The variance of the raw detector voltage varies in a way which is indicative of the amount of cavitation activity in the object. This is because each cavitation bubble produces a pulse of ultrasound when it collapses. Therefore the more bubbles that are present, and collapsing, the higher the ultrasound intensity, and hence the higher the variance in the pressure signal from the sensor 12 at ultrasound frequencies. Since cavitation acts as a mechanism for converting ultrasound energy into heat energy in the object, the temperature of the object would be expected to increase with the amount of cavitation activity, and experimentally it can be shown, as seen in FIG. 2, that the relationship between cavitation activity, as measured by sensory voltage variance, and temperature rise, is approximately linear. The results shown in FIG. 2 were obtained for the system of FIG. 1 with a tissue-mimicking gel as the subject.

Referring to FIG. 3, in one experiment using the system of FIG. 1, porcine subcutaneous fat was exposed to ultrasound and the temperature increase monitored over time for various different amplitudes of acoustic wave over different periods of time, giving different values of total acoustic energy delivered. FIG. 3 shows the results from measurements over the first second of exposure, FIG. 4 the results over the first two seconds of exposure, FIG. 5 the results over the first three seconds, and FIG. 6 the results over the first four seconds. As can be seen, in each case, the temperature increase is again related to the total acoustic energy detected by the sensor by a roughly linear relationship.

The results of FIGS. 2 and 3 to 6 show that the temperature rise in a subject varies approximately linearly with the detected cavitation activity. However, as discussed above, temperature rise is a useful parameter for some applications but not directly indicative of the permanent effects of treatment on tissue. If the frequencies of the ultrasound produced by cavitation are investigated, it can be shown that this varies with the state of the tissue in which the cavitation is being produced. Referring to FIG. 7, the spectral content of ultrasound generated in tissue at different temperatures and different degrees of denaturation were investigated by computational modelling. The second highest peak at most frequencies, marked 'a' is the level of emissions when the tissue is at 37° C. The highest peak at most frequencies, marked 'b' is the level of emissions when the tissue is at 60° C. This is higher as the tissue will generally have become more fluid, so more cavitation will occur, but the spectral shape is similar. The peak marked 'c' is where the tissue is denatured but still at 72° C. It can be seen that the overall cavitation activity is much lower, and is more concentrated at lower frequencies. The peaks marked 'd' are where the tissue is denatured and cooled to 37° C. Because of the increased stiffness of the tissue in that state the cavitation levels are lower again, and concentrated even more at lower frequencies. From this it can be seen that the spectral content of ultrasonic emissions can be used as an indicator of the state of tissue being treated. For a passive cavitation detector, the frequency content of the acoustic emissions from cavitation can be determined directly from the frequency content of the detector output signal.

Figure 8:
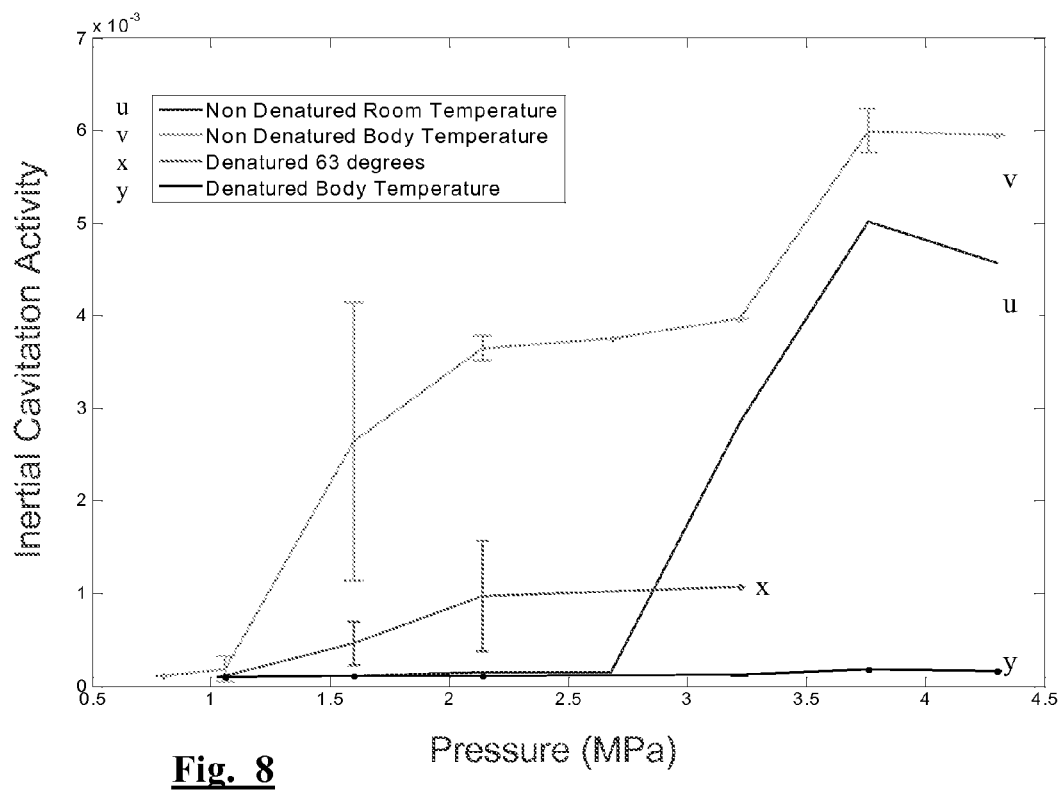
FIG. 8 is a graph showing changes in the cavitation threshold (i.e. the minimum pressure required to instigate inertial cavitation) during denaturation of tissue.

A further factor which varies with the nature, or state, of the tissue, is the cavitation threshold, i.e. the minimum acoustic pressure that is needed to start cavitation. Referring to FIG. 8 the system of FIG. 1 was controlled so as to increase the ultrasound intensity gradually over time and monitor the resulting level of inertial cavitation activity as measured by the variance of the sensor signal. This was repeated for tissues at different temperatures and different states. The results are as shown in FIG. 8. The line u shows the results for non-denatured tissue at room temperature, the line v shows the results for non-denatured tissue at body temperature, the line w shows the results for denatured tissue at 63° C., and the line x shows the results for denatured tissue at body temperature. As can be seen for non-denatured tissue at room temperature, the cavitation threshold pressure is around 2.7 MPa and cavitation increases rapidly with pressure up to about 3.7 MPa, for non-denatured tissue at body temperature, the cavitation threshold pressure is around 1.1 MPa and cavitation increases with pressure up to about 3.7 MPa, for denatured tissue at 63° C., the cavitation threshold pressure is around 1.1 MPa and cavitation increases much more slowly with pressure up to about 2.1 MPa and then levels off, and for denatured tissue at body temperature, no significant change of cavitation is seen for pressures up to about 4.4 MPa.

When performing therapeutic treatment of tissue the system of FIG. 1 is arranged to receive and analyse the signals from the detector 12 and control the HIFU transmitter in response to those signals, for example varying parameters of the control signal to the transmitter so as to vary parameters of the ultrasound generated in response to variation in parameters of the detection signals. For example when used in tissue ablation the controller 16 is arranged to monitor and control the temperature to which the tissue is heated, and also arranged to monitor changes in the nature of the tissue, such as denaturation, and to vary the ultrasound generated in response to that, for example by stopping the ultrasound when the desired effects have been achieved.

Figure 9:
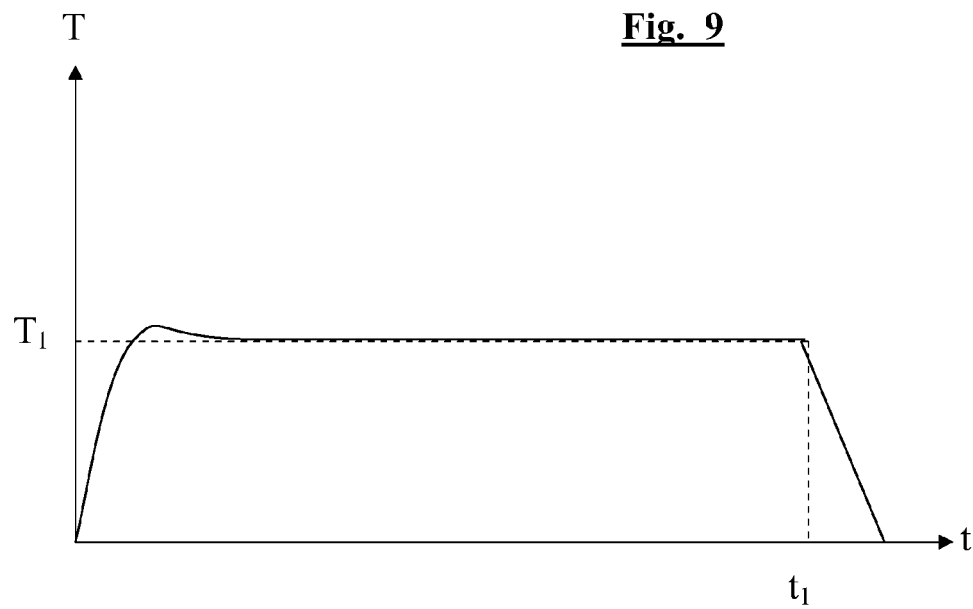
FIG. 9 is a graph showing variation in temperature over time in an object being treated by the system of FIG. 1.

In order to control the temperature of the tissue, the controller has stored in it, for example as a look-up table, a record of the relationship of FIG. 2 relating values of the detector signal variance to values of temperature. The controller identifies a target temperature for the tissue, either as input by a user or as stored in memory. Then during treatment the controller is arranged to control the transducer 11 to generate pulses of ultrasound by producing a drive signal for the transducer 11, and is also arranged to control the amplitude and frequency of the ultrasound and the width and frequency of the pulses, so as to control the corresponding parameters of the ultrasound generated. The controller 16 varies one or more of these parameters in response to changes in the variance of the detector signal in order to maintain the variance at a level corresponding to a target temperature or temperature range of the tissue. The control of tissue temperature can take a number of forms depending on the therapeutic process being performed. In one simple control mode the controller determines when the temperature reaches a predetermined level, or remains above a predetermined threshold for a predetermined time, and in response turns off the ultrasound or reduces the ultrasound power. This provides a basic safety function. Referring to FIG. 9, in a more sophisticated control mode the controller has stored in memory a target temperature which may be fixed or may vary over time. In this example the target temperature is shown as a broken line and has a fixed value of $T_1$ for a time period $t_1$. During treatment the temperature of the tissue is measured by monitoring the detector signal variance, and the amplitude, or frequency, or pulse width, of the ultrasound varied, using a feedback control loop, so as to maintain the temperature as close as possible to the target temperature. For example the ultrasound is applied at full power and the temperature is monitored as it initially rises until it reaches the target temperature. Then the power is varied in response to variations in temperature so as to maintain the desired temperature. Then when the target temperature has been maintained for the target time, the power is switched off and the temperature falls steadily, as shown in the solid line.

During operation of the system, the estimated temperature of the tissue can be displayed on the display 18, for example as a simple figure or as a plot of temperature as a function of time. This allows a user to monitor the temperature of the tissue in real time as the treatment is in progress, and to take any appropriate action that may be necessary, such as overriding the normal operation of the system to stop the treatment or adjust the power of the ultrasound transmission.

In another mode of operation the controller 16 is arranged to monitor the viscoelastic properties of the tissue during treatment so as to determine how the treatment is progressing, and when the treatment has been completed. From FIGS. 7 and 8 it can be seen that, as tissue is heated and denatured, both the frequency content of the ultrasound emissions from cavitation, and the threshold cavitation pressure will change as the tissue changes. These effects can both be monitored and used to determine when a desired change in the tissue has been achieved, so that ultrasound delivery can be stopped or modified at the appropriate time. Therefore the controller 16 is arranged to analyse continually the frequency spectrum of the detected ultrasound. When the ultrasound is pulsed this can be done by analysing the frequency content of the ultrasound detected during or after each transmitted pulse. It can also be arranged to vary, for example to rapidly increase, the amplitude, and hence power, of the ultrasound over time, and to monitor the detector signals and determine from them the time, and hence the peak ultrasound pressure, at which cavitation starts and the way in which cavitation varies with peak pressure. This can again be done for each pulse of the pulse width modulated (PWM) ultrasound signal to obtain different measurements over time. From these measurements, and using for example look-up tables stored in memory which relate the measured values to the viscoelastic properties of the tissue, those viscoelastic properties can be monitored during therapy, and the ultrasound from the transducer 11 can be varied during therapy. For example, the ultrasound transducer 11 may be turned off when a desired change in the tissue properties is detected. As well as, or instead of, controlling the ultrasound output from the transducer 11 in response to changes in the detector signals, the controller 16 can be arranged to output a drive signal to the display to control the display 18 so as to indicate these changes to a user, so that the user can control the ultrasound manually. For example the controller can be arranged to generate a display that varies with the viscoelastic properties of the tissue, so that a user can determine when they have changed sufficiently and stop the treatment at that point.

In a modification to the embodiment described above, rather than having a look-up table relating the properties of the tissue to specific values of the measured parameters, the controller 16 may have stored therein definitions of one or more reference variations in the detection signals that correspond to respective variations in the tissue properties. The controller 16 is then arranged to control the ultrasound transmission in response to variations in the sensor signals. These reference variations can be expressed, for example, in terms of percentage variations in either the frequency content or threshold cavitation pressure. For example the controller 16 can be arranged to turn the ultrasound off when the reference change is detected. This has the advantage that the system does not need to be so accurately calibrated as if absolute values are used as the reference.

In another embodiment of the invention, the controller 16 is replaced by another form of processor which processes the detector signals and outputs a sensor signal that varies with the parameter of the object, for example with its temperature or viscoelastic properties, but this not used to control the ultrasound transducer. Instead the ultrasound transducer is controlled by a dedicated controller, and the sensor signal from the processor is used simply to drive a display indicative of the parameter of the object, or as an input to a further controller for a separate system or process.

It will be appreciated that the embodiments described above have a number of benefits. They allow properties of the tissue to be monitored continuously during treatment so that changes in tissue properties can be detected in real time and the ultrasound radiation controlled in response, either manually, or automatically through a feedback control loop.

The embodiments described above relate to the sensing of processes controlled by therapeutic ultrasound systems for tissue ablation, but the procedures are directly extendable to sensing and optimizing other therapeutically desirable bioeffects and could also extend to applications outside the biomedical arena (for example ultrasound cleaning baths, cavitation control in nuclear reactors, etc.).

Any or all of the embodiments described above can be combined together into a single system arranged to perform the functions of each of them.

Figure 10:
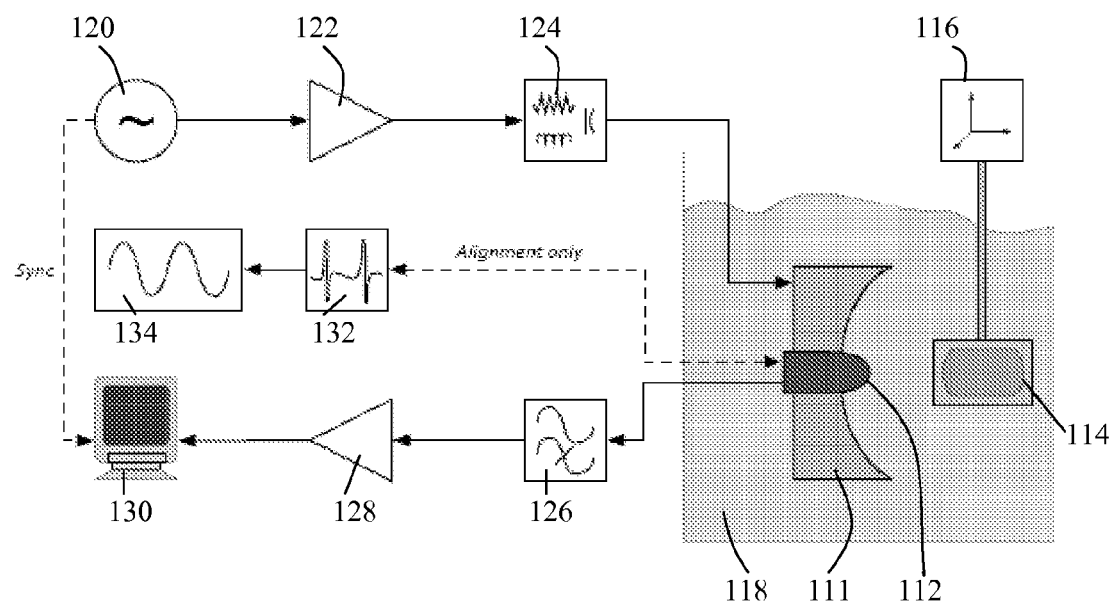
FIG. 10 is a diagram of a therapeutic ultrasound system according to a further embodiment of the invention.

Referring to FIG. 10 a test system according to a further embodiment of the invention comprises an ultrasound transducer 111, in this a case spherically focussed HIFU transducer with an insonation frequency of 1.067 MHz and a focal length of 62.6 mm arranged to transmit a focused beam of ultrasound, and a passive ultrasound detector 112, in this case a broadband, focussed transducer with a centre frequency of 15 MHz and a focal length of 75.0 mm, arranged coaxially with the transducer 111 and at its centre so that it can detect ultrasound from the focal point of the transducer 111. A sealed tissue holder 114 is located at the focal point of the transducer 111 and is supported on a motorized 3D positioning system 116 which is arranged to adjust the position of the tissue holder in three dimensions. The transducer 111 and tissue holder 114 are submerged in a water tank 118 containing degassed, deionised water kept at 37° C. using an immersion heater. In a therapeutic system the transducer 111 and detector 112 would be adapted for contact with the body of the subject.

A function generator 120 is arranged to generate driving signals for the transducer 111. The output from the function generator 120 is connected to the input of a 55 dB high-power RF amplifier 122 which is arranged to amplify the driving signal. The output of the amplifier 122 is input to a transducer specific matching network 124 arranged to maximize power transfer from the transducer, and the output of the matching network is arranged to drive the transducer 111. The output from the detector 112 is fed via a 2 MHz high pass filter 126 to remove seep-through at the fundamental frequency of the HIFU transducer 111 and a broadband amplifier 128 with a gain of 25 to a data acquisition unit 130 comprising a 14-bit digitiser, a data acquisition circuit, and a processor for processing the acquired data and generating an output derived from processing the data, and an output device, such as a screen, for outputting to a user the results of the data processing. An ultrasonic pulser receiver 132 and an oscilloscope 134 are also connected to the detector 112 for alignment purposes.

In order to test the system of FIG. 10, a sample of ox liver tissue measuring 9 cm by 9 cm in cross section and 4 cm in depth was cut out of the organ, avoiding large veins and blood vessels where possible. To maintain as much clinical relevance as possible, the tissue was cut such that the front face of the block retained the capsule surrounding the organ. During exposures, this face was positioned nearest to the HIFU transducer 111, as would be the case during an in vivo HIFU treatment. The excised block of liver was immersed in 4 L of Dulbecco's Phosphate Buffered Saline (PBS). The tissue and PBS were degassed at 0.2 bar for 30 minutes, after which the liver was sealed in the tissue holder 114 which had the same dimensions. When transferring the tissue to the holder 114, care was taken to ensure that the liver was surrounded by degassed PBS at all times so as to minimise the ingress of air bubbles. The holder was constructed such that ultrasound could pass freely between the front and back faces of the tissue block via thin, acoustically transparent windows made of biaxially oriented polyethylene terephthalate film (commonly referred to as boPET or Mylar).

The holder 114 was aligned such that the focus of the HIFU transducer 111 was positioned 2 cm deep into the tissue for each exposure. All exposures were carried out using quasi-continuous HIFU with a 95% duty cycle and a pulse length of 50 ms. The duty cycle was chosen to allow for passive localisation of any cavitating microbubbles using time-of-flight information acquired while the HIFU transducer is turned off. Exposures in the same tissue sample were carried out in grids with a spacing of 1 cm between adjacent points.

To measure acoustic emissions from the focus during each exposure, the transducers 111, 112 were aligned confocally and coaxially by using a brass ball with a diameter of 6.4 mm as an acoustic target. It should be noted that the sensitive focal volume of the detector transducer is frequency-dependent. The −3 dB focal volume of the passive detector at various multiples of the HIFU frequency and for a speed of sound of 1500 m/s are listed in Table 1.

TABLE 1

−3 dB focal volume of the detector transducer at various multiples of the insonation frequency (1.067 MHz), assuming a speed of sound of 1500 m/s.

| Frequency (MHz) | 1.067 | 2.134 | 3.201 | 4.268 | 5.335 |
|---|---|---|---|---|---|
| Harmonic | Fundamental | 2nd | 3rd | 4th | 5th |
| −3 dB Focal Volume (mm$^3$) | 6380 | 1110 | 380 | 173 | 93.4 |

Data acquisition was performed by acquiring traces of 40,000 samples of data at a sampling frequency of 100 MHz. Each new trace was acquired as soon as the previous trace was written out of the buffer; typical delays between consecutive traces were on the order of 5-10 ms. To measure background noise, acquisition was started 2 s before each HIFU exposure, and continued for 2 additional seconds after the HIFU transducer was turned off. FIG. 11 illustrates the data acquisition protocol with an example set of traces from a single HIFU exposure (FIG. 11a), a single trace from this set (FIG. 11b), the spectral content of this trace (FIG. 11c), and the spectrogram of the entire HIFU exposure (FIG. 11d). The spectrogram is an effective tool for visualising how the frequency content of the passively monitored signal evolves over the course of the exposure.

Post-Exposure Lesion Volume Measurement

After the tissue had been exposed to HIFU, the sample was removed from its holder 114 and sliced transversely at a depth of 2 cm, through the central plane of the HIFU focal region, by making use of a guiding slit in the holder. A photograph of the tissue after this cut, on the side furthest from the transducer. The diameter d of each lesion cross-section was measured using vernier callipers. The tissue was then sliced in the axial plane passing through the centre of each lesion, and the length l of each lesion was also measured using the callipers.

To determine lesion volume, the shape of the lesions was approximated as a prolate spheroid (i.e. an ellipsoid with equal equatorial radii). This approximation was motivated by visual inspection of the lesions and has also been used in other studies.

Using this approximation, the diameter d of the lesion cross-section corresponds to the equatorial diameter and the length l of the lesion corresponds to the polar diameter, giving a lesion volume V of $$V = \frac{\pi \cdot d^2 \ell}{6} \tag{1}$$

Detector Algorithm

Figure 12:
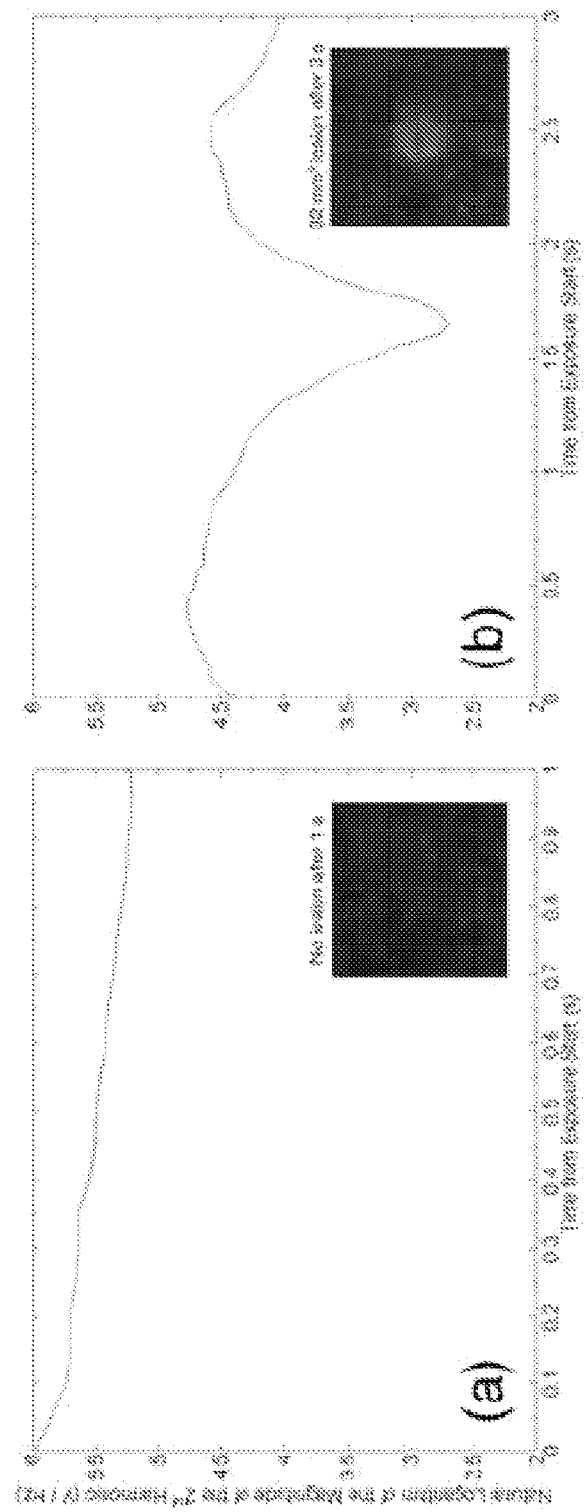
FIGS. 12a and 12b are plots of the magnitude of passively monitored ultrasound signal at integer harmonics of the insonation frequency without and with the formation of lesions.

All data were analysed in MATLAB release 2009a (The Mathworks, Natick, Mass., USA). Initial examination of the spectrograms associated with each exposure suggested that, in exposures that generated lesions, the magnitude of the passively monitored acoustic signal would temporarily decrease by an order of magnitude or more at integer multiples of the insonation frequency, as illustrated in FIG. 12. FIG. 12a shows variation of the $2^{nd}$ harmonic of the insonation frequency over time during a 1 s period when no lesions are generated, and FIG. 12b shows the variation over a 3 s period during which lesions are generated. As can be seen, the generation of lesions is associated with a dip in the magnitude of the $2^{nd}$ order harmonic. Based on this observation, an algorithm was devised to detect the presence or absence of this feature in the signal and implemented in MATLAB.

Figure 13:
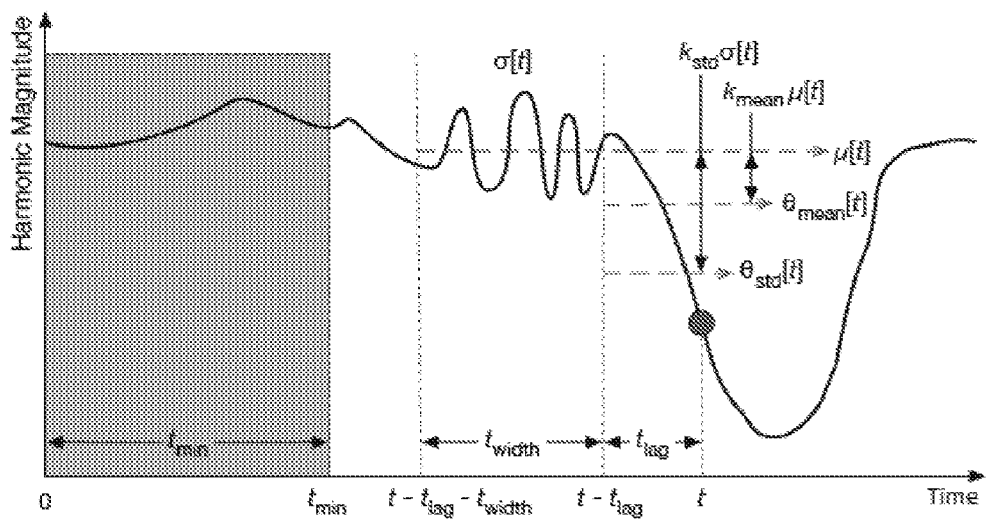
FIG. 13 shows the parameters used in a detection algorithm arranged to detect minima in the harmonic plots in the system of FIG. 10.

The algorithm is illustrated in FIG. 13. To begin with, a spectrogram of the signal is computed using a Short Time Fourier Transform, as illustrated in FIG. 11d. The harmonics of interest are then extracted directly from the spectrogram. In FIG. 11d, this would correspond to isolating single horizontal lines in the plot closest to the frequencies associated with each harmonic.

After all harmonics of interest have been extracted, the mean μ and standard deviation σ of the amplitude of each harmonic are calculated over a window having a width of $t_{width}$ and a lag of $t_{lag}$ with respect to the current time, as illustrated in FIG. 13. Thus, at a given time t, the mean and standard deviation in the window may be computed using the equations $$\mu[t] = \frac{\sum_{\tau \in [t - t_{lag} - t_{width}, t - t_{lag}]} h(\tau)}{f_s \cdot t_{width}} \tag{2}$$

and

-continued $$\sigma[t] = \sqrt{\frac{\sum_{\tau \in [t-t_{lag}-t_{width}, t-t_{lag}]} h^2(\tau)}{f_s \cdot t_{width}} - \mu^2[t]} \quad (3)$$

Where:

h is the magnitude over time of harmonic being analysed, and $f_s$ is the sampling frequency (hence, $f_s \cdot t_{width}$ is the number of points in the window).

It should be noted that Equations 2 and 3 can only be applied once a time of $t_{min} = t_{width} + t_{lag}$ has elapsed, since this is the minimum time required to establish the window. However, as described below, for the parameter values selected in this study, no lesioning occurs during this initial time period.

To identify dips such as those shown in FIGS. 12b and 13, two thresholds are established based on the values of the mean μ and the standard deviation σ associated with each harmonic. The first threshold, $\theta_{mean}$, is defined as a percentage of the mean, while the second threshold, $\theta_{std}$, is set to a certain number of standard deviations below the mean.

These thresholds are illustrated in FIG. 13 and may be computed using the equations $$\theta_{mean}[t] = (1 - k_{mean})\mu[t] \quad (4)$$

and $$\theta_{std}[t] = \mu[t] - k_{std}\sigma[t] \quad (5)$$

where $k_{mean}$ and $k_{std}$ are positive numbers and can be set as constants to tune the algorithm. A dip is identified when the harmonic falls below the smaller of these two thresholds and subsequently rises above this same threshold at a later time. The processor in the data acquisition unit 130 is therefore arranged to perform this algorithm on the acquired data. For example it can be arranged to repeat the algorithm repeatedly during the insonation so as to detect when a dip in energy of the harmonics of interest occurs.

Detector Parameter Selection and Performance Assessment

For simplicity, and because detection was performed entirely offline in the study described above, ideal (non-causal) bandpass filters with a passband width of 30 kHz were used to obtain the spectrogram and extract the harmonics. Since the fundamental frequency was filtered out prior to signal acquisition as noted previously, the lowest harmonic examined was the 2nd one. Also, the highest harmonic that could be reliably distinguished from noise in all exposures was found to be the 5th one; hence, higher harmonics than this were not considered.

The values that were selected for the parameters $t_{width}$, $t_{lag}$, $k_{mean}$, and $k_{std}$ are given in Table 2. As noted previously, the detector is only applied once a time of at least $t_{min} = t_{width} + t_{lag}$ has elapsed since the start of the exposure. For the parameter values shown in Table 2, the value of this minimum elapsed time is 0.6 s.

TABLE 2

Parameter values selected for the dip detector.

| Parameter Name | Value Selected | Quantity Affected |
|---|---|---|
| $t_{width}$ | 0.5 s | Width of the detector window |
| $t_{lag}$ | 0.1 s | Lag of the detector window |
| $k_{mean}$ | 0.2 | Threshold based on the mean |

TABLE 2-continued

Parameter values selected for the dip detector.

| Parameter Name | Value Selected | Quantity Affected |
|---|---|---|
| $k_{std}$ | 1.5 | Threshold based on the standard deviation |

Detector performance was assessed by comparing the output of the detector to the post exposure measurement of lesion volume. For this purpose, lesions were deemed to have formed if their volume was at least 10 mm³. The four possible cases that can occur when comparing the output of the detector to the lesion formation assessment are listed in Table 3.

TABLE 3

Detector performance assessment categories.

| Lesion Measurement | Detector Output | Result Classification |
|---|---|---|
| Lesion | Dip | True positive (correct) |
| No lesion | No dip | True negative (correct) |
| Lesion | No dip | False negative (error) |
| No lesion | Dip | False positive (error) |

Results and Discussion

Lesion Size

Figure 14:
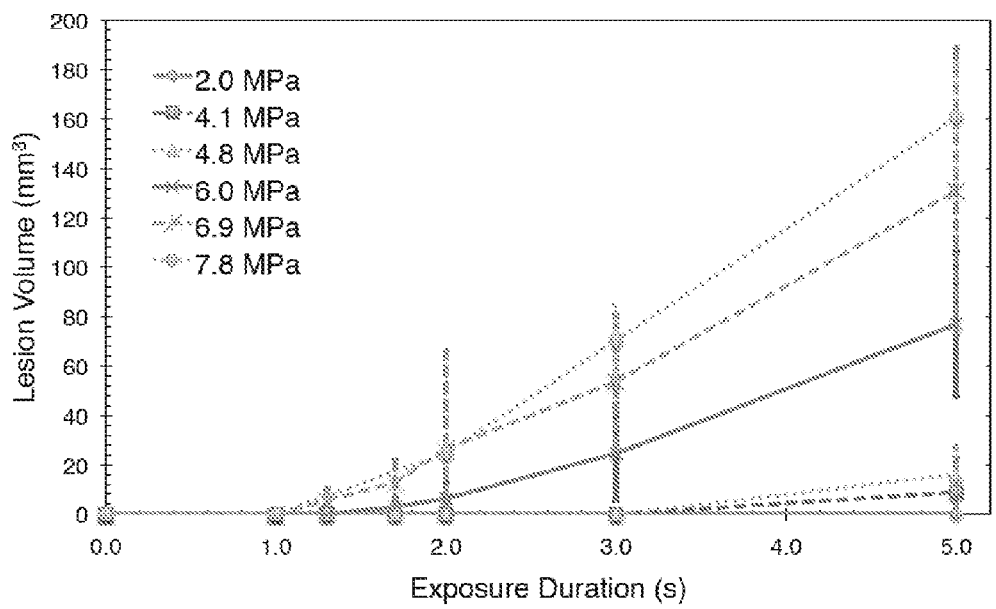
FIG. 14 is a graph showing average lesion volume as a function of exposure time and peak rarefaction pressure amplitude in the system of FIG. 10.

FIG. 14 shows the variation in lesion volume with both exposure time and peak rarefaction pressure. The error bars in the figure result mainly from the difficulty in obtaining precise measurements of lesion volumes using manual slicing. The variability between tissues from different animals as well as inhomogeneities within the same block of tissue also act as sources of error. Nevertheless, in spite of these factors, lesion volume increases with both exposure time and peak rarefaction pressure as would be expected. This justifies the use of the manual slicing method as a straightforward means of determining whether or not lesioning has occurred.

FIG. 14 also shows that no lesions form at any of the pressures tested if the tissue is only exposed for 1 s. Thus, no events of significance are missed in the first 0.6 s before detection begins.

Detector Performance and Sources of Error

Figure 15:
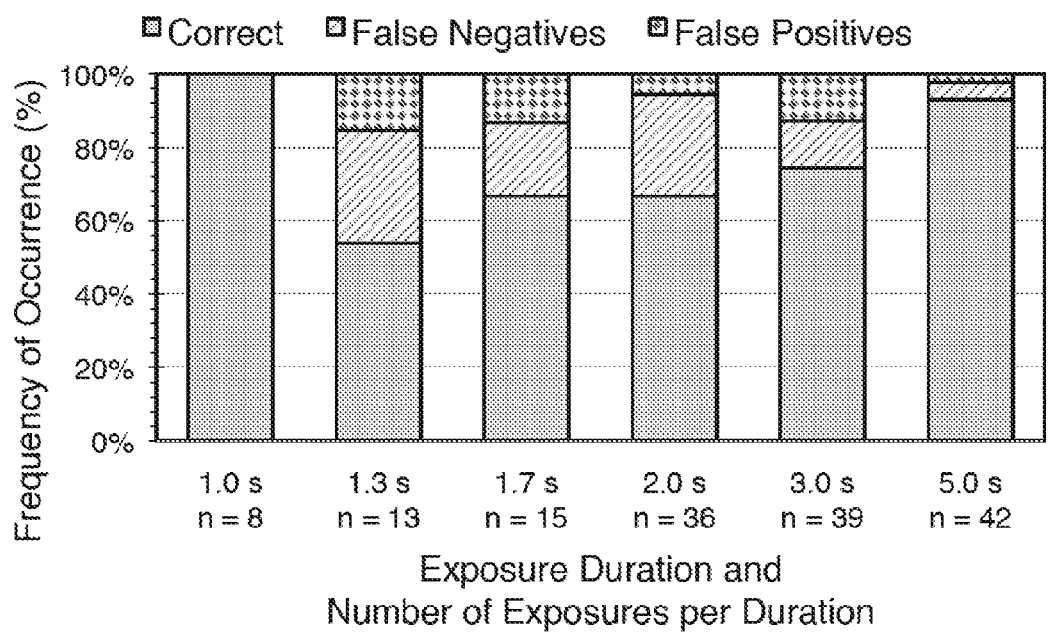
FIG. 15 is a graph showing performance statistics of the detector of FIG. 10.

FIG. 15 displays the performance of the detector for each exposure duration tested, along with the number of exposures performed for each duration. The figure shows that the detection rate varies with exposure time, with the best performances occurring for 1 s and 5 s exposures, respectively the shortest and longest durations tested. The weakest performance occurs at 1.3 s; after this time, it can be seen that the detection rate generally increases with exposure duration.

The 100% detection rate for the 1 s exposures is consistent with the result that no lesions form for this exposure duration, as shown in FIG. 14. This demonstrates that the detector functions correctly in the period preceding the onset of lesioning. Similarly, 92% of the 5 s dataset is correctly classified, with only 1 false positive in 42 exposures. As can be seen in FIG. 14, most of the 5 s exposures resulted in large lesions. Hence, the high detection rate for this exposure duration shows that the detector performs well in regimes that cause significant lesioning.

On the other hand, at 1.3 s the detection rate is only 53%, the lowest of all exposure times. The decreased detector performance at this exposure duration is likely because lesions are just beginning to form around this time. This explanation is supported by a number of observations that can be inferred from the results. Firstly, the detection rate generally increases with exposure duration after 1.3 s, which is consistent with more lesions having had sufficient time to form properly and subsequently be identified by the detector. Secondly, as shown in FIG. 14, the volume of the lesions caused by exposures less than 2 s long is generally less than about 25 mm. In comparison, Table 1 shows that the −3 dB focal volume of the detector transducer ranges in size from 93 to 6380 mm$^3$ across the frequencies that were examined. Thus, a significant proportion of the lesions that were created in the shorter exposures may have simply been too small to detect relative to the sensitive volume of the detection transducer. Finally, for the exposures lasting 1.3 s, 1.7 s, and 2 s, the detector exhibits a high proportion of false negatives (where lesioning occurs but no dip is detected). This may indicate that lesions are forming soon after the HIFU has been turned off: during this time, there are no longer acoustic emissions to monitor from the focus, but the tissue continues to experience thermal damage until the heat deposited by the HIFU dissipates. In fact, in 29% (7 of 24) of false negatives, the start of a dip was observed close to the end of the exposure, but it appeared that the signal did not have time to return above the threshold prior to the end of the exposure. Hence, for these exposures, it is likely that the signal is not recorded during the time period in which the lesion actually forms, thereby resulting in a false negative rather than successful detection.

In summary, the detector performs well for exposures where significant lesioning occurs, without raising undue false alarms before lesions have started to form. The detection rate drops in the transition between these two states, where small lesions have just begun to appear. However, this is to be expected for the reasons mentioned previously, and in practice may be avoided by using a suitably long exposure. This strategy, as well as other ways of mitigating the effect of detector errors in a clinical setting, is discussed below.

Practical Consequences of Detector Errors and Mitigation Strategies

In practice, false negatives (where lesioning occurs but no dip is detected) are undesirable due to the misinformation conveyed to the operator. However, this type of error does not present a danger to successful treatment in a clinical setting, as the surgeon could simply perform additional exposures, potentially up to a certain maximum number in the relatively unlikely event that no dip appeared in any of the subsequent tries. Using this strategy, false negatives would essentially result in overtreatment, which is no worse than the currently employed method of monitoring for hyperechogenic regions on postexposure B-mode images. On the other hand, false positives (where a dip is detected but no lesion has formed) present a potentially greater danger in a clinical scenario, as these could lead to undertreatment.

FIG. 15 demonstrates that exposures between 1 and 2 s long experience especially high proportions of this type of error. As mentioned previously, this is likely because lesions are just beginning to form in this time window for the frequencies and pressures used in this work. A straightforward solution to reduce the false positive rate is therefore to establish an appropriate minimum treatment time—for example, 2 s in this study—based on previous experience or empirical data. An additional consideration specific to this study is the imprecision of the manual slicing technique used to assess lesioning, as some lesions may have been missed or been too small to detect. Moreover, combining the present detector with other real-time lesion detection methods, such as Amplitude-Modulated Harmonic Motion Imaging and passive cavitation mapping, could serve to decrease the false positive rate even further.

Potential Underlying Physical Mechanisms

While the results shown in FIG. 15 demonstrate that the presence of dips in harmonics correlates well with the formation of lesions, further investigation into the physical mechanisms that underlie this phenomenon is required. Based on previous work, it is likely that a change in the viscoelastic or other material properties of the tissue is implicated in the physical explanation. For example, the dip in the magnitude of the received signal could be due to the tissue absorbing energy as it transitions from reversible heat-induced stiffness change to the irreversible change in stiffness that marks the onset of tissue denaturation.

Due to the high peak rarefaction pressures employed in this study, it is also plausible that acoustic cavitation is occurring and playing a role in changing the acoustic emissions from the focus during the exposure. If acoustic cavitation is involved, one possibility is that the cavitating microbubbles are acting as nonlinear scatterers due to changes in their cavitation dynamics, which are in turn caused by changes in the viscoelastic properties of the surrounding medium. Alternatively, the microbubbles could be functioning as linear scatterers of an initially linear wave propagating in a nonlinear medium (i.e. there are harmonics present by the time the wave reaches the bubbles). In this case, the dips would be caused by a change in the nonlinearity coefficient (B/A) of the surrounding tissue as it stiffens due to irreversible denaturation. A confounding factor in distinguishing these two possibilities is the difficulty in separating the effects of nonlinear propagation (i.e. effects caused by the changes in the material properties of the medium) from those caused by changing bubble dynamics: in fact, both types of effect may be present simultaneously. Further experiments are required to ascertain the role of acoustic cavitation in causing the observed correlation between dips in the signal harmonics and lesioning in the tissue.

However it will be appreciated that the design of an effective monitoring system is not affected by the lack of a clear physical explanation of the processes taking place in the tissue. Also it will be appreciated that any one or more of the signal parameter measurements described above for the system of FIG. 1 can also be included in the system of FIG. 10, and that while they can be indicative of cavitation processes, they may also be affected partly or wholly by other processes.

Further Embodiments and Modifications

In the study described above, the detector was only implemented and used offline. An online implementation would entail a number of additional considerations, including appropriate filter selection. However, provided that the magnitude of the frequency components between the harmonics remains orders of magnitude below the harmonics themselves, and that consecutive harmonics are well spaced out, any notch filter with a sufficiently rapid rolloff would be capable of extracting a given harmonic. The filtered signal would correspond approximately to a sinusoid at the frequency of the harmonic located in the passband of the filter. Straightforward demodulation in the form of envelope detection would then provide the time-varying magnitude of the harmonic during the exposure.

The study described above demonstrates that lesioning in ex vivo ox liver tissue is highly correlated with the presence of pronounced local minima ("dips") in the harmonics of the acoustic signal emitted from the HIFU focus. A detector based on this observation can enable real-time monitoring of lesion formation in ex vivo ox liver, and could therefore also be used for in vivo monitoring of denaturation of tissue in patients. The detector can monitor tissue denaturation directly, rather than relying on indirect indicators such as hyperechogenicity or temperature. Such a detector can therefore provide a low-cost means of effectively monitoring clinical HIFU treatments passively and in real time.

The invention claimed is:

1. A sensing system to sense a parameter of an object, the sensing system comprising a transducer arranged to generate pressure waves directed at the object, at least one pressure wave detector arranged to detect cavitation in the object and output detection signals, and a controller arranged to receive the detection signals from the at least one detector, to process the detection signals to measure a signal parameter of the detection signals that varies with the parameter of the object, wherein the controller has stored therein a record of either a relationship between the parameter of the object and the signal parameter, or at least one reference variation in the signal parameter that corresponds to a respective variation in the parameter of the object, and the controller is arranged to use the record to generate a sensor output that varies in response to changes in the signal parameter, wherein either:
   (a) the parameter of the object is temperature, and the signal parameter is arranged to vary with a level of cavitation activity in the object;
   (b) the parameter of the object is a viscoelastic parameter, and the controller is arranged to determine a cavitation threshold pressure from the signal parameter;
   (c) the parameter of the object is a viscoelastic parameter, and the signal parameter is a parameter of the frequency content of the detection signals; or
   (d) the parameter of the object is a presence of lesions, and the signal parameter is a parameter of the spectral content of the detection signals.

2. A system according to claim 1 wherein the sensor output is arranged to control the transducer to vary an output of the transducer in response to changes in the sensor output.

3. A system according to claim 1 further comprising a feedback device arranged to provide feedback to a user, wherein the sensor output is arranged to control the feedback device and to vary the feedback in response to changes in the sensor output.

4. A system according to claim 1 wherein the controller is arranged to define a target range of the signal parameter, and to change the sensor output in response to the signal parameter being outside the target range.

5. A system according to claim 1 wherein the signal parameter is a variance of the detection signals.

6. A system according to claim 1 wherein the controller is arranged to monitor how the signal parameter changes in response to changes in the sensor output.

7. A system according to claim 1 wherein the signal parameter is a timing parameter.

8. A system according to claim 7 wherein the signal parameter is indicative of a cavitation threshold of the object.

9. A method of sensing a parameter of an object comprising:
   generating pressure waves directed at the object;
   sensing cavitation in the object using at least one pressure wave detector arranged to output detection signals;
   measuring a signal parameter of the detection signals that varies with a parameter of the object;
   accessing a record of either a relationship between the parameter of the object and the signal parameter, or at least one reference variation in the signal parameter that corresponds to a respective variation in the parameter of the object, and
   using the record to generate a sensor output; wherein either:
   (a) the parameter of the object is temperature, and the signal parameter is arranged to vary with a level of cavitation activity in the object;
   (b) the parameter of the object is a viscoelastic parameter, and a cavitation threshold pressure is determined from the signal parameter;
   (c) the parameter of the object is a viscoelastic parameter, and the signal parameter is a parameter of the frequency content of the detection signals; or
   (d) the parameter of the object is a presence of lesions, and the signal parameter is a parameter of the spectral content of the detection signals.

10. A method according to claim 9 wherein the sensing output varies in response to changes in the signal parameter.

* * * * *